US00PP24646P2

(12) United States Plant Patent
Blom

(10) Patent No.: US PP24,646 P2
(45) Date of Patent: Jul. 15, 2014

(54) ***CHRYSANTHEMUM* PLANT NAMED 'ZANMURYDER'**

(50) Latin Name: ***Chrysanthemum×morifolium* Ramat.**
Varietal Denomination: Zanmuryder

(71) Applicant: Chrysanthemum Breeders Association Research B.V., Aalsmeer (NL)

(72) Inventor: Wilhelmus Bernardus Blom, Leimuiden (NL)

(73) Assignee: Chrysanthemum Breeders Association Research B.V., Valkenburg (NL)

( * ) Notice: Subject to any disclaimer, the term of this patent is extended or adjusted under 35 U.S.C. 154(b) by 0 days.

(21) Appl. No.: 13/694,694

(22) Filed: Dec. 26, 2012

(51) Int. Cl.
*A01H 5/00* (2006.01)

(52) U.S. Cl.
USPC ..... Plt./293

(58) Field of Classification Search
USPC ..... Plt./293
See application file for complete search history.

*Primary Examiner* — Anne Grunberg
(74) *Attorney, Agent, or Firm* — Steptoe & Johnson LLP

(57) ABSTRACT

A *Chrysanthemum* plant named 'Zanmuryder' characterized by its small sized blooms with dark red ray florets and prolific branching; natural season flowering date August 27 (week 35); blooming for a period of 5 weeks.

3 Drawing Sheets

Botanical designation: *Chrysanthemum×morifolium* Ramat.

Cultivar denomination: 'Zanmuryder'.

BACKGROUND OF THE INVENTION

The present invention relates to a new and distinct cultivar of *Chrysanthemum* plant, botanically known as *Chrysanthemum×morifolium* Ramat., commercially known as a garden mum, and hereinafter referred to by the cultivar denomination 'Zanmuryder'. 'Zanmuryder' is a product of a breeding and selection program for outdoor pot mums (garden mums) which had the objective of creating new cultivars with a double type inflorescence, a natural season flowering date around August 27 (week 35), blooming for a period of 5 weeks. 'Zanmuryder' is a seedling resulting from a cross of the female parent id 16733 with an unknow male parent. Plants of the new cultivar 'Zanmuryder' differ from plants of the female parent in plant vigor; plants of the seedling are less vigorous than those of the female parent.

The new and distinct cultivar was discovered and selected as a flowering plant by Wilhelmus Bernardus Blom on a cultivated field in Rijsenhout, The Netherlands in 2009. The first act of asexual production of 'Zanmuryder' was accomplished when vegetative cuttings from the initial selection in 2009 were propagated further in a controlled environment in Rijsenhout, The Netherlands. The new cultivar has been found to retain its distinctive characteristics through successive propagations.

BRIEF DESCRIPTION OF THE DRAWINGS

The present invention of a new and distinct variety of *Chrysanthemum* (of about 14 weeks) is shown in the accompanying drawings, the color being as nearly true as possible with color photographs of this type.

DESCRIPTION OF THE INVENTION

Figure 1:
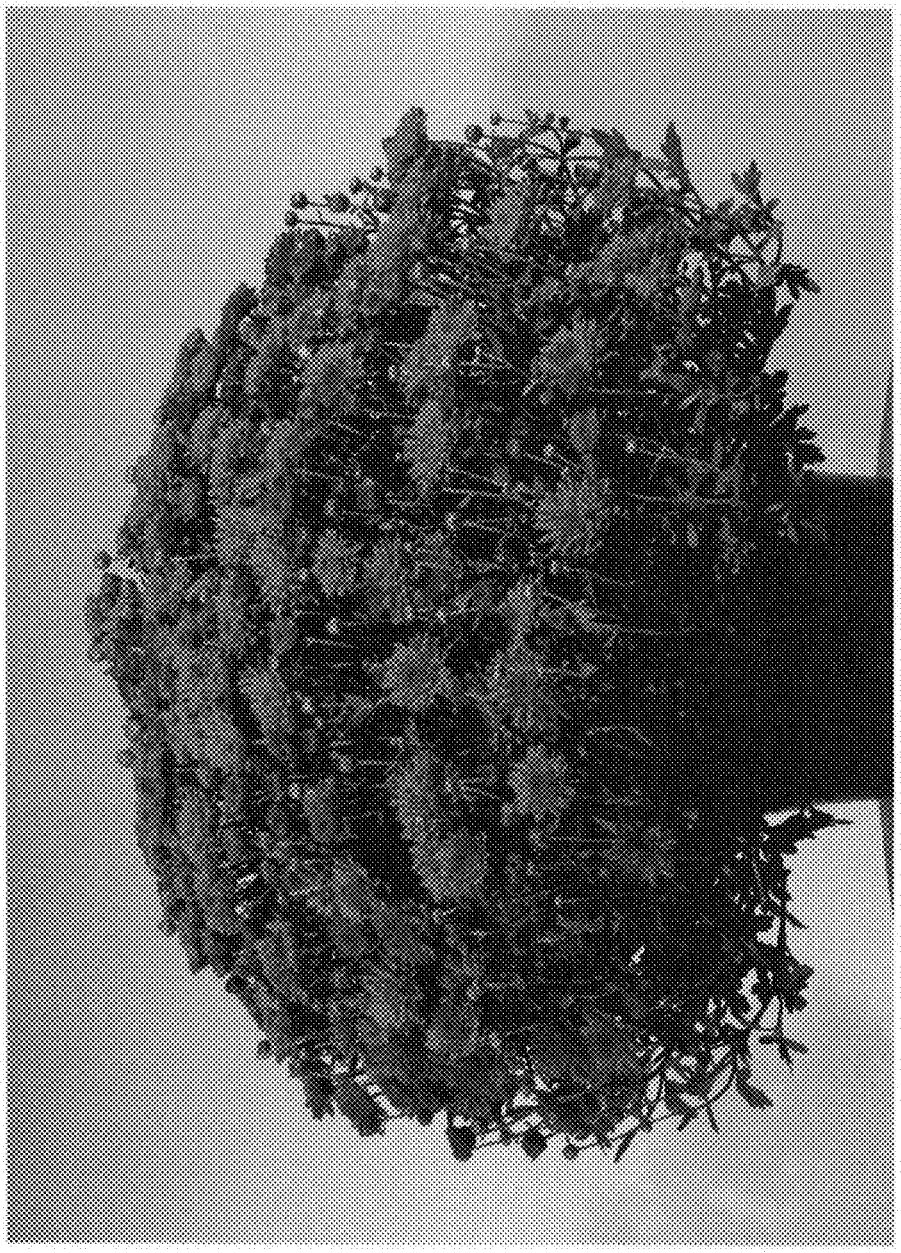
FIG. 1 shows a plant of the cultivar in full bloom.
Figure 2:
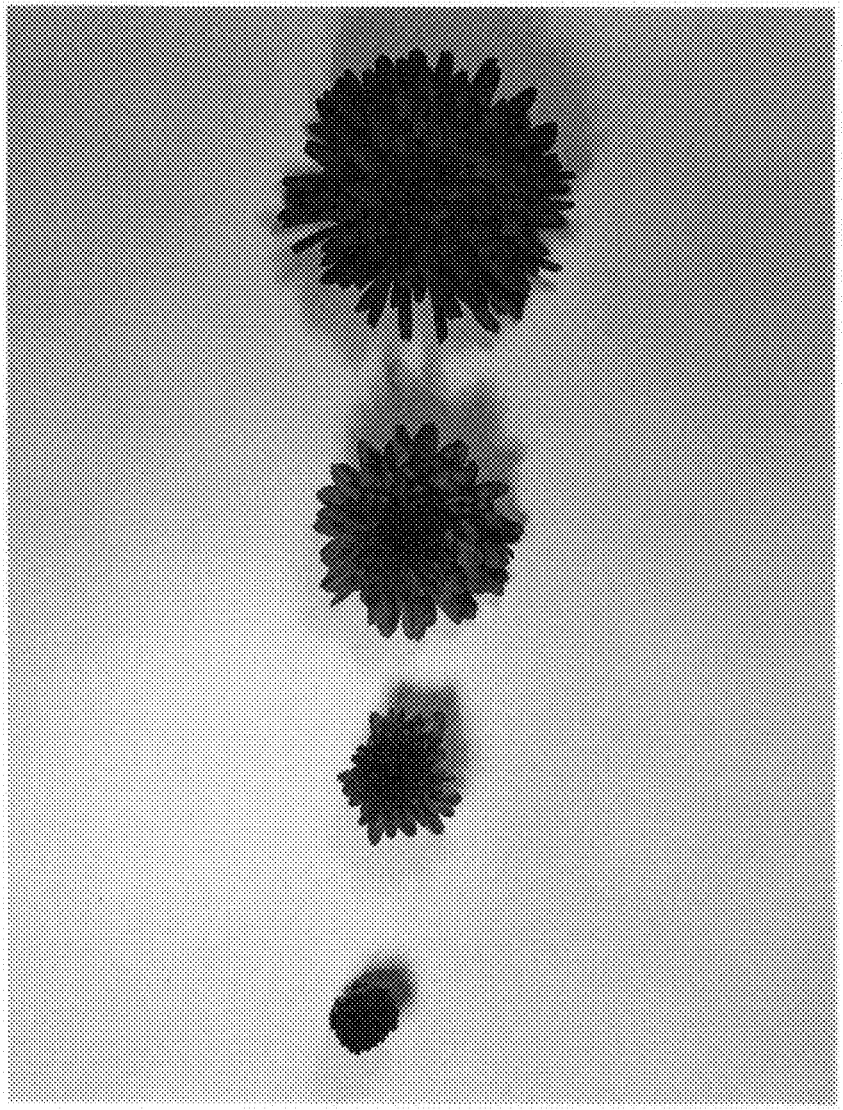
FIG. 2 shows the various stages of bloom of the new cultivar.
Figure 3:
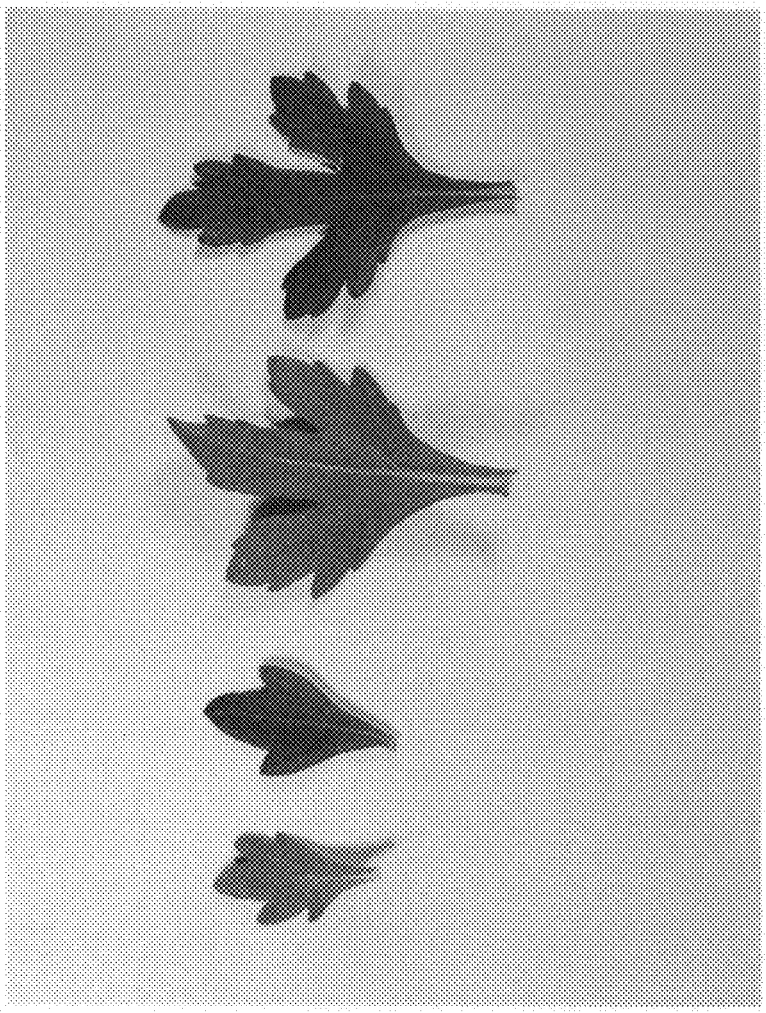
FIG. 3 shows the various stages of foliage of the new cultivar.

The observations and measurements were gathered from plants grown out door in Rijsenhout, The Netherlands under natural day length and temperature and planted in week 23 in 2012. The natural blooming date of this crop was August 27 (week 35). The average height of the plants was 30 cm. No growth retardants were used. No tests were done on disease or insect resistance or susceptibility. No tests were done on cold or drought tolerance. This new variety produces small sized blooms with dark red ray florets blooming for a period of 5 weeks.

From the cultivars known to inventor the most similar existing cultivar in comparison to 'Zanmuryder' is 'Manakin' (U.S. Plant Pat. No. 11,521). When 'Zanmuryder' and 'Manakin' are being compared the following differences are noticed: (1) Inflorescence type. And (2) Color ray-florets. (1) Inflorescence type in 'Zanmuryder' is double, while it is daisy in 'Manakin'. (2) Ray-florets in 'Zanmuryder' are more purple colored than those of 'Manakin'.

The following is a description of the plant and characteristics that distinguish 'Zanmuryder' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

Botanical Description of *Chrysanthemum ×morifolium* Ramat. 'Zanmuryder'

| Bud | |
|---|---|
| Size: | Small; cross-section 7 mm, height 4 mm |
| Shape: | Round |
| Texture: | Pubescent |
| Outside color: | Greyed-green 191A |

TABLE 1-continued

Botanical Description of *Chrysanthemum* ×*morifolium* Ramat. 'Zanmuryder'

| | |
|---|---|
| Phyllaries | |
| Number: | 36, arranged in 3 rows |
| Shape: | Elliptic |
| Apex: | Acute |
| Base: | Truncate |
| Margin: | Entire |
| Color: | Upper side: Green 138A<br>Lower side: Green 143C |
| Length and width: | 4-5 mm; 2 mm |
| Texture: | Pubescent |
| Inflorescences | |
| Type: | Double |
| Height: | 1.5 cm |
| Diameter: | 3.5-4 cm |
| Peduncle length: | 6.5-8 cm |
| Peduncle color: | Green 138B |
| Peduncle diameter: | 2 mm |
| Peduncle texture: | Pubescent |
| Number per branch: | Approx. 6-8 inflorescences |
| Duration of flowering: | 5 weeks |
| Seeds: | Produced in small quantities, ovate, Greyed-brown 199A, length 1.5 mm, diameter 0.5 mm |
| Fragrance: | Faint *chrysanthemum* odor |
| Color inflorescences | |
| Center of inflorescence: | Immature stage: Red-purple 60A; Mature stage: Red-purple 60A |
| Color of upper side of ray florets: | Red-purple 60A |
| Color of lower side of ray florets: | Greyed-yellow 161C at base to Greyed-purple 184B at tip |
| Tonality from distance: | A garden *mum* with dark red blooms |
| Color of ray florets after aging of the plant: | Greyed-purple 185A |
| Ray florets | |
| Texture: | Upper and lower side smooth |
| Number: | 180-200 |
| Shape: | Elliptic |
| Apex: | Dentate |
| Base: | Attenuate |
| Cross-section: | Flat |
| Longitudinal axis: | Straight |
| Length of corolla tube: | 2 mm |
| Ray floret margin: | Entire |
| Ray floret length: | 1.2-2.1 cm |
| Ray floret width: | 2-3 mm |
| Ratio length/width: | High |
| Disc florets | Absent |
| Receptacle | |
| Color: | Yellow-green 145D |
| Shape: | Domed raised |
| Height: | 8 mm |
| Diameter: | 4 mm |
| Reproductive Organs | |
| Androecium: | Absent |
| Pollen: | Absent |
| Gynoecium: | Present on ray florets |
| Style color: | Yellow-green 154C |
| Style length: | 3 mm |
| Stigma color: | Yellow 7A |

TABLE 1-continued

Botanical Description of *Chrysanthemum* ×*morifolium* Ramat. 'Zanmuryder'

| | |
|---|---|
| Stigma width: | 1 mm |
| Ovary: | Enclosed in calyx |
| Plant | |
| Form: | Grown as a spray type pot mum, outdoor raised and mounded |
| Growth habit: | Spherical shape |
| Growth rate: | Medium |
| Height: | 30 cm |
| Width: | 40 cm |
| Stem color: | Greyed-brown 199A |
| Stem strength: | Strong |
| Stem brittleness: | Not brittle |
| Stem anthocyanin coloration: | Present, Greyed-purple 185C |
| Internode length: | 1.5-3 cm |
| Length of lateral branch: | From top to bottom 16-18 cm |
| Lateral branch color: | Green 137 C |
| Lateral branch, attachment: | Strong |
| Lateral branch diameter: | 3-4 mm |
| Branching (average number of lateral branches): | Prolific with 8-10 breaks after pinching |
| Natural season blooming date: | August 27 (week 35) |
| Foliage | |
| Leaf color: | Upper side: Green 137A; Lower side: Green N138B |
| Color midvein: | Upper side: Yellow-green 147D;<br>Lower side: Yellow-green 148D |
| Size: | Small; length 3-5 cm, width 1.5-3.5 cm |
| Quantity (number per lateral branches): | 14-16 |
| Shape: | Elliptic |
| Texture upper side: | Sparsely pubescent |
| Texture under side: | Pubescent |
| Venation arrangement: | Palmate |
| Shape of margin: | Serrated |
| Shape of base of sinus between lateral lobes: | Rounded |
| Margin of sinus between lateral lobes: | Diverging |
| Shape of base: | Attenuate |
| Apex: | Mucronulate |
| Petiole length: | 0.5-1.5 cm |
| Petiole diameter: | 2 mm |
| Petiole color: | Yellow-green 147D |

TABLE 2

Differences with the comparison variety, when grown under identical conditions

| | 'Zanmuryder' | 'Manakin' |
|---|---|---|
| Inflorescence type | double | daisy |
| Color ray-florets | Red-purple 60A | Red 46A |

I claim:

1. A new and distinct *Chrysanthemum* plant named 'Zanmuryder' as described and illustrated.

* * * * *